United States Patent
Blaney et al.

[11] Patent Number: 6,110,479
[45] Date of Patent: *Aug. 29, 2000

[54] MICROPOROUS FILM CONTAINING A MICROBIAL ADSORBENT

[75] Inventors: Carol Ann Blaney; William Francis Cartwright, both of Roswell; David Craige Strack, Canton, all of Ga.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/956,924

[22] Filed: Oct. 23, 1997

Related U.S. Application Data

[63] Continuation of application No. 08/469,052, Jun. 6, 1995, abandoned.

[51] Int. Cl.[7] ................................................. A01N 25/34
[52] U.S. Cl. ........................ 424/402; 424/404; 428/198; 428/286; 428/315.5; 428/315.7; 428/315.9; 428/317.9; 428/312.8
[58] Field of Search .................... 424/402, 404; 428/198, 286, 315.5, 315.7, 315.9, 317.9, 312, 8

[56] References Cited

U.S. PATENT DOCUMENTS

| | | | |
|---|---|---|---|
| 3,276,944 | 10/1966 | Levy | 161/150 |
| 3,316,136 | 4/1967 | Pufahl | 156/160 |
| 3,338,992 | 8/1967 | Kinney | 264/24 |
| 3,341,394 | 9/1967 | Kinney | 161/72 |
| 3,502,538 | 3/1970 | Petersen | 161/150 |

(List continued on next page.)

FOREIGN PATENT DOCUMENTS

| | | |
|---|---|---|
| 803714 | 1/1969 | Canada . |
| 1255978 | 6/1989 | Canada . |
| 1272115 | 7/1990 | Canada . |
| 2025186 | 9/1990 | Canada . |
| 2028495 | 4/1991 | Canada . |
| 2032061 | 6/1991 | Canada . |
| 2033844 | 7/1991 | Canada . |
| 1305300 | 7/1992 | Canada . |
| 1312426 | 1/1993 | Canada . |
| 1317424 | 5/1993 | Canada . |

(List continued on next page.)

OTHER PUBLICATIONS

Database WPI, Week 8636, Derwent Publications Ltd., London, GB; AN 86–236752 & JP–A–61 167 550 (Toyo Chemical KK), Jul. 29, 1986, Abstract.

Database WPI, Week 8849, Derwent Publications Ltd., London, GB, AN 88–351188 & JP–A–63 264 336 (Asahi Chemical Ind KK), Nov. 1, 1988, Abstract.

Database WPI, Week 8120, Derwent Publications Ltd., London, GB; AN 81–35328d & JP–A–56 032 241 (Mitsui Toatsu Chem Inc.), Apr. 1, 1981, Abstract.

Database WPI, Week 8621, Derwent Publications Ltd., London, GB; AN 86–135042/21 & JP–A–61 072 543 (Komatsu Seiren KK), Apr. 14, 1986, Abstract.

(List continued on next page.)

*Primary Examiner*—S. Mark Clardy
*Assistant Examiner*—Kathryne E. Shelborne
*Attorney, Agent, or Firm*—Nelson Mullins Riley & Scarborough

[57] ABSTRACT

Disclosed is a film which includes a microbial adsorbent and which is capable of providing a microbial barrier while still being able to allow passage of water vapor. The film has first and second surfaces and defines least one microporous passageway allowing communication, through the film, between the first and second surfaces. In particular, a portion of the microporous passageway is defined by the microbial adsorbent so that microbes attempting to pass through the film via a passageway must pass in close proximity to the microbial adsorbent. This arrangement allows the microbial adsorbent to interdict the microbe by adsorbing it and prohibiting its passage through the film.

41 Claims, 3 Drawing Sheets

U.S. PATENT DOCUMENTS

| | | | |
|---|---|---|---|
| 3,502,763 | 3/1970 | Hartmann | 264/210 |
| 3,542,615 | 11/1970 | Dobo et al. | 156/181 |
| 3,676,242 | 7/1972 | Prentice | 156/62.4 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,909,009 | 9/1975 | Cvetko et al. | 274/37 |
| 3,935,363 | 1/1976 | Burkholder et al. | 428/281 |
| 3,949,128 | 4/1976 | Ostermeier | 428/152 |
| 3,973,063 | 8/1976 | Clayton | 428/35 |
| 4,041,203 | 8/1977 | Brock et al. | 428/157 |
| 4,042,740 | 8/1977 | Krueger | 428/138 |
| 4,081,301 | 3/1978 | Buell | 156/164 |
| 4,087,486 | 5/1978 | Fielding et al. | 260/897 |
| 4,100,324 | 7/1978 | Anderson et al. | 428/288 |
| 4,104,404 | 8/1978 | Bieler et al. | 428/35 |
| 4,144,370 | 3/1979 | Boulton | 428/233 |
| 4,185,135 | 1/1980 | Huff | 428/96 |
| 4,254,175 | 3/1981 | Kubat et al. | 428/213 |
| 4,278,524 | 7/1981 | Kadija | 204/252 |
| 4,297,157 | 10/1981 | Van Vliet | 156/164 |
| 4,297,408 | 10/1981 | Stead et al. | 428/240 |
| 4,300,967 | 11/1981 | Sigl | 156/164 |
| 4,307,143 | 12/1981 | Meitner | 252/91 |
| 4,318,408 | 3/1982 | Korpman | 128/287 |
| 4,340,563 | 7/1982 | Appel et al. | 264/518 |
| 4,341,213 | 7/1982 | Cohen | 128/284 |
| 4,348,444 | 9/1982 | Craig | 428/137 |
| 4,379,192 | 4/1983 | Wahlquist et al. | 428/156 |
| 4,430,381 | 2/1984 | Harvey et al. | 428/284 |
| 4,434,258 | 2/1984 | Schumacher et al. | 524/13 |
| 4,443,513 | 4/1984 | Meitner et al. | 422/195 |
| 4,446,189 | 5/1984 | Romanek | 428/152 |
| 4,449,977 | 5/1984 | Korpman | 604/366 |
| 4,454,055 | 6/1984 | Richman et al. | 252/194 |
| 4,472,328 | 9/1984 | Sugimoto et al. | 264/41 |
| 4,500,670 | 2/1985 | McKinley et al. | 524/445 |
| 4,522,203 | 6/1985 | Mays | 128/132 D |
| 4,525,407 | 6/1985 | Ness | 428/138 |
| 4,568,341 | 2/1986 | Mitchell et al. | 604/368 |
| 4,579,729 | 4/1986 | Schoenthal et al. | 423/626 |
| 4,585,604 | 4/1986 | Okuyama et al. | 264/41 |
| 4,595,629 | 6/1986 | Mays | 428/286 |
| 4,606,964 | 8/1986 | Wideman | 428/152 |
| 4,606,970 | 8/1986 | Sharps, Jr. | 428/301 |
| 4,626,252 | 12/1986 | Nishizawa et al. | 604/370 |
| 4,650,481 | 3/1987 | O'Connor et al. | 604/380 |
| 4,656,062 | 4/1987 | Harriett | 427/397.8 |
| 4,657,802 | 4/1987 | Morman | 428/152 |
| 4,681,793 | 7/1987 | Linman et al. | 428/138 |
| 4,692,368 | 9/1987 | Taylor et al. | 428/137 |
| 4,704,238 | 11/1987 | Okuyama et al. | 264/41 |
| 4,707,398 | 11/1987 | Boggs | 428/224 |
| 4,720,415 | 1/1988 | Vander Wielen et al. | 428/152 |
| 4,721,511 | 1/1988 | Kupits | 8/188 |
| 4,725,473 | 2/1988 | Van Gompel et al. | 428/156 |
| 4,741,944 | 5/1988 | Jackson et al. | 428/152 |
| 4,748,978 | 6/1988 | Kamp | 128/156 |
| 4,758,617 | 7/1988 | Tanioku et al. | 524/413 |
| 4,761,324 | 8/1988 | Rautenberg et al. | 428/198 |
| 4,793,956 | 12/1988 | Nogiwa et al. | 264/41 |
| 4,814,124 | 3/1989 | Aoyama et al. | 264/41 |
| 4,822,350 | 4/1989 | Ito et al. | 604/372 |
| 4,826,516 | 5/1989 | Matsuoka et al. | 55/388 |
| 4,837,079 | 6/1989 | Quantrille et al. | 428/288 |
| 4,877,679 | 10/1989 | Leatherman et al. | 428/224 |
| 4,879,078 | 11/1989 | Antoon, Jr. | 264/41 |
| 4,883,549 | 11/1989 | Frost et al. | 156/161 |
| 4,902,544 | 2/1990 | Kim et al. | 428/36.1 |
| 4,921,653 | 5/1990 | Aoyama et al. | 264/41 |
| 4,929,303 | 5/1990 | Sheth | 156/209 |
| 4,935,287 | 6/1990 | Johnson et al. | 428/198 |
| 4,981,747 | 1/1991 | Morman | 428/198 |
| 4,983,450 | 1/1991 | Yanagihara et al. | 428/283 |
| 5,011,698 | 4/1991 | Antoon, Jr. et al. | 426/395 |
| 5,051,189 | 9/1991 | Farrah | 210/679 |
| 5,069,907 | 12/1991 | Mixon et al. | 424/445 |
| 5,110,769 | 5/1992 | Welsh et al. | 501/12 |
| 5,114,781 | 5/1992 | Morman | 428/198 |
| 5,116,662 | 5/1992 | Morman | 428/198 |
| 5,143,679 | 9/1992 | Weber et al. | 264/288.8 |
| 5,169,712 | 12/1992 | Tapp | 428/315.5 |
| 5,174,231 | 12/1992 | White | 112/420 |
| 5,190,533 | 3/1993 | Blackburn | 604/367 |
| 5,208,098 | 5/1993 | Stover | 428/284 |
| 5,244,716 | 9/1993 | Thornton et al. | 428/198 |
| 5,261,899 | 11/1993 | Visscher et al. | 604/367 |
| 5,296,290 | 3/1994 | Brassington | 428/300 |
| 5,300,192 | 4/1994 | Hansen et al. | 162/184 |
| 5,328,758 | 7/1994 | Markell et al. | 428/281 |
| 5,336,552 | 8/1994 | Strack et al. | 428/224 |
| 5,352,216 | 10/1994 | Shiono et al. | 604/312 |
| 5,405,644 | 4/1995 | Ohsumi et al. | 427/2.31 |
| 5,409,761 | 4/1995 | Langley | 428/198 |
| 5,695,871 | 12/1997 | Tallentire et al. | 428/320 |

FOREIGN PATENT DOCUMENTS

| | | |
|---|---|---|
| 066672B1 | 12/1982 | European Pat. Off. |
| 084903A3 | 8/1983 | European Pat. Off. |
| 116865A1 | 8/1984 | European Pat. Off. |
| 192965A1 | 9/1986 | European Pat. Off. |
| 297538A3 | 1/1989 | European Pat. Off. |
| 302597A2 | 2/1989 | European Pat. Off. |
| 309073A2 | 3/1989 | European Pat. Off. |
| 323629A2 | 7/1989 | European Pat. Off. |
| 330783A3 | 9/1989 | European Pat. Off. |
| 360929A1 | 4/1990 | European Pat. Off. |
| 403187 A1 | 8/1990 | European Pat. Off. |
| 391661A3 | 10/1990 | European Pat. Off. |
| 399439A3 | 11/1990 | European Pat. Off. |
| 409567A2 | 1/1991 | European Pat. Off. |
| 444671A3 | 2/1991 | European Pat. Off. |
| 422561A3 | 4/1991 | European Pat. Off. |
| 257280B1 | 9/1991 | European Pat. Off. |
| 482918A3 | 4/1992 | European Pat. Off. |
| 307116B1 | 8/1993 | European Pat. Off. |
| 556749A1 | 8/1993 | European Pat. Off. |
| 599425A1 | 6/1994 | European Pat. Off. |
| 620111A1 | 10/1994 | European Pat. Off. |
| 691203 | 1/1996 | European Pat. Off. |
| 2260716 | 5/1974 | Germany. |
| 43 11 422 | 10/1994 | Germany. |
| 62-282003 | 12/1987 | Japan. |
| 1-144431 | 6/1989 | Japan. |
| 2-036938 | 2/1990 | Japan. |
| 4-227260 | 8/1992 | Japan. |
| 793072 | 6/1979 | South Africa. |
| 1519172 | 7/1978 | United Kingdom. |
| 1575010 | 9/1980 | United Kingdom. |
| 2023493B | 10/1982 | United Kingdom. |
| 2115702A | 9/1983 | United Kingdom. |
| 2155853A | 12/1984 | United Kingdom. |
| 2272917A | 6/1994 | United Kingdom. |
| 2285408A | 7/1995 | United Kingdom. |
| 2290052A | 12/1995 | United Kingdom. |
| 87/01400 | 3/1987 | WIPO. |
| 88/01570 | 3/1988 | WIPO. |
| 90/06228 | 6/1990 | WIPO. |
| 91/02643 | 3/1991 | WIPO. |
| 91/11324 | 8/1991 | WIPO. |
| 93/11725 | 6/1993 | WIPO. |
| 93/11726 | 6/1993 | WIPO. |

| | | |
|---|---|---|
| 93/21013 | 10/1993 | WIPO . |
| 93/22995 | 11/1993 | WIPO . |
| 94/09193 | 4/1994 | WIPO . |
| 94/20298 | 9/1994 | WIPO . |
| 95/10940 | 4/1995 | WIPO . |
| 95/16562 | 6/1995 | WIPO . |

OTHER PUBLICATIONS

Database WPI, Section Ch. Week 9517, Derwent Publications Ltd., London, GB; AN 95–128842 XP002014413 & JP,A,07 054 208 (Teijin Ltd.), Feb. 28, 1995, See Abstract.

Database WPI, Section Ch, Week 9412, Derwent Publications Ltd., London, GB; AN 94–097914 XP002014436 & JP,A,06 049 253, Feb. 22, 1994, See Abstract.

Database WPI, Section Ch, Week 9247, Derwent Publications Ltd., London, GB; AN 92–385722 XP002014437 & JP,A,04 284 235, Oct. 8, 1992, See Abstract.

Database WPI, Section Ch, Week 9145, Derwent Publications Ltd., London, GB; AN 91–329942 XP002014438 & JP,A,03 221 540, Sep. 30, 1991, See Abstract.

"Effects of Bentonite Clay Solids on Poliovirus Concentration From Water By Microporous Filter Methods," Applied and Environmental Microbiology, Apr. 1985, pp. 795–798.

Farrah & Erdos, 1991, "The production of antibacterial tubing, sutures, and bandages by in situ precipitation of metallic salts," Dept. of Microbiology & Cell Science, U. of Florida, pp. 445–449.

"Inactivation of Bacteria by Solids Coated with Magnesium Peroxide," Asghari & Farrah, *Journal of Environmental Science and Health*, 1993, pp. 779–793.

*The United States Pharmacopeia USP XXII—The National Formulary NF XVII*, Jan. 1, 1990, p. 1902.

*Kirk–Othmer Encyclopedia of Chemical Technology*, 3rd ed., vol. 6, pp. 207–209, John Wiley & Sons, NY, Mar. 1979.

*The Condensed Chemical Dictionary*, 10th ed., Gessner G. Hawley, Van Nostrand Reinhold Co., NY, 1981, p. 115.

"Specialty Clay Product Summary," Technical Data Sheet, Volclay MPS 1, IC–590, May 1992, American Colloid Company.

Farrah & Erdos, 1991, "The Production of Antibacterial Tubing, Sutures, and Bandages By in Situ Precipation of Metallic Salts, " Dept. of Microbiology & Cell Science, U. of Florida, pp. 445–449.

"Inactivation of Bacteria By Solids Coated With Magnesium Peroxide," Asghari & Farrah, *Journal of Environmental Science and Health*, 1993, pp. 779–793.

*The United States Pharmacopeia USP XXII—The National Formulary NF XVII*, Jan. 1, 1990, p. 1902.

*Kirk–Othmer Encyclopedia of Chemical Technology*, $3^{rd}$ ed., vol. 6, pp. 207–209, John Wiley & Sons, NY, Mar. 1979.

*The Condensed Chemical Dictionary*, $10^{th}$ ed., Gessner G. Hawley, Van Nostrand Reinhold Co., NY, 1981, p. 115.

"Specialty Clay Product Summary," Technical Data Sheet, Volclay MPS, 1, IC–590, May 1992, American Colloid Company.

MICROPOROUS FILM CONTAINING A MICROBIAL ADSORBENT

This application is a continuation of application Ser. No. 08/469,052 entitled "MICROPOROUS FILM CONTAINING A MICROBIAL ADSORBENT" and filed in the U.S. Patent and Trademark Office on Jun. 6, 1995. The entirety of this application is hereby incorporated by reference. Now abandoned.

FIELD OF THE INVENTION

The field of the present invention encompasses film materials which possess antimicrobial characteristics.

BACKGROUND OF THE INVENTION

Films have been traditionally used to provide barrier properties in single-use items including, but not limited to, articles of clothing in general, protective apparel, healthcare related products including surgical drapes, gowns, and sterile wrap and personal care absorbent products such as diapers, training pants, incontinence garments, sanitary napkins, bandages, and the like. In personal care absorbent products such as infant diapers and adult incontinence products, films are used as the outer covers with the purpose of preventing body wastes from contaminating the clothing, bedding, and other aspects of the surrounding environment of use. In the area of protective apparel including hospital gowns, films are used to prevent exchange of microorganisms between the wearer and the patient. These films are usually one to two mils in thickness and have a basis weight of approximately 0.7 to 1.5 ounces per square yard. Polyolefin films are most commonly used in such areas.

One of the significant disadvantages in the utilization of films as barrier materials in most, if not all, of these types of products is that the films do their job too well. That is, they form a complete barrier. Complete barriers of this type create an entirely new problem in that they block the egress of water vapor from the person or item which the film enwraps. Accordingly, those wearing garments formed from such materials tend to rapidly become quite uncomfortable due to a build-up of water vapor which is given off by the individual but not allowed to pass through the film. The water vapor remains between the individual and the garment or item made from the material. The individual rapidly develops a feeling of being "sweaty" or "sticky" as the relative humidity in that confined area builds up and water vapor condenses therein.

In response to this problem, those of skill in the art have attempted to manufacture protective garments and other items where passage of microbes is undesirable from materials which allow the passage of water vapor. Such materials include, for example, nonwoven webs and laminates thereof as discussed in detail in U.S. Pat. No. 4,041,203 to Brock et al. This patent is hereby incorporated herein by reference in its entirety.

Microporous varieties of films, either by themselves or incorporated in laminates, have also been used in such products in an attempt to provide articles with more garment-like attributes, such as the ability to reduce the relative humidity underneath the garment, thus maintaining a higher degree of comfort for the wearer.

However, the use of nonwoven webs and/or microporous films in certain protective apparel has not been without difficulties. For example, utilization of such materials has generated concerns about their ability to prevent transfer of microorganisms because the size of microorganisms such as virus and bacteria are typically much smaller than the pores of microporous films. Nonwoven web materials, typically, also are characterized by passageways therethrough which, while they may retard the progress of microbes, do not guarantee complete barrier properties with respect to them. For these reasons, neither of these arrangements has proven to be completely satisfactory in view of the fact that they do not form a complete barrier for microbes.

Therefore, there remains a distinct need for a material which allows the passage of water vapor therethrough while effectively forming a barrier to the passage of small pathogens such as viruses, bacteria, cysts and nematodes. If such a material were a film, it could be used as one layer of a laminate with a nonwoven material to provide an overall material which would have effective microbial barrier properties, breathability (that is, allow passage of an adequate amount of water vapor) and tactile feel.

OBJECTS OF THE INVENTION

Accordingly, it is an object of the present invention to provide a microporous film which allows the passage of water vapor while still being an effective barrier material for microbes such as viruses, bacteria, cysts and nematodes.

It is a further object of the present invention to provide a microporous film which also allows the passage of water vapor, is an effective barrier for microbes such as viruses, bacteria, cysts and nematodes and, upon being exposed to a generally aqueous liquid, forms a physical barrier to the passage of such liquid therethrough in the area limited to such exposure.

It is yet another object of the present invention to provide a laminate of such microporous films with one or more nonwoven webs.

These and other objects and the broad scope of applicability of the present invention, will become apparent to those of skill in the art from the details given hereinafter. However, it should be understood that the detailed description of the presently preferred embodiments of the present invention is given only by way of illustration because various changes and modifications well within the spirit and scope of the invention will become apparent to those of skill in the art in view of this detailed description.

SUMMARY OF THE INVENTION

In response to the aforementioned difficulties encountered by those of skill in the art, we have invented a film which includes a microbial adsorbent and which is capable of providing a microbial barrier while still being able to allow passage of water vapor. The film has first and second surfaces and defines at least one microporous passageway allowing communication, through the film, between the first and second surfaces. Such communication, in some embodiments, allows the passage of water vapor through the film. In particular, a portion of the microporous passageway is defined by the microbial adsorbent so that microbes attempting to pass through the film via a passageway must pass in close proximity to the microbial adsorbent. This arrangement allows the microbial adsorbent to interdict the microbe by adsorbing it and prohibiting its passage through the film.

In some embodiments the film may be formed from a thermoplastic polymer. For example, the thermoplastic polymer may be selected from the group including polyolefins, polyamides, polyesters and copolymers and blends in any combination of these and/or any other suitable material. For example, the polyolefin may be selected from the group consisting of polypropylenes, polyethylenes, polybutylenes and copolymers and blends thereof. The polyethylene may be linear low density polyethylene. In other embodiments, the film may be a solvent cast film formed from any conventional material known to those in the art as being appropriate for the formation of such solvent cast films.

By specifically tailoring the type of microbial adsorbent present in the film, the film may be adapted to adsorb viruses, bacteria, cysts or nematodes or any or all of these. Naturally the film may be adapted to adsorb specific types of viruses, bacteria, cysts, nematodes etc., depending upon the use to which it is to be assigned.

In certain embodiments, the film may be designed to not only act as a filter for microbes as a result of the presence of the microbial adsorbent but may also be designed to act as a physical (mechanical) barrier to fluids attempting to pass therethrough. To this end, the microbial adsorbent utilized may be one which, in the presence of a generally aqueous fluid, increases its volume at least 1.5 times in no more than 120 seconds. For example, the microbial adsorbent may be one which, in the presence of a generally aqueous fluid, increases its volume at least 1.5 times in no more than 60 seconds. More particularly, the microbial adsorbent may be one which, in the presence of a generally aqueous fluid, increases its volume at least 1.5 times in no more than 15 seconds. Even more particularly, the microbial adsorbent may be one which, in the presence of a generally aqueous fluid, increases its volume at least 2 times in no more than 1 second. In the event such a microbial adsorbent is utilized, the adsorbent will, upon being contacted with the generally aqueous fluid, increase in size and swell. The swelling serves to block the microporous passageway with which the microbial adsorbent is in close proximity. Blockage of the passageway creates a physical barrier within the microporous passageway with the consequence that no further liquid can pass.

An alternative manner by which physical blockage may be obtained, if the microbial adsorbent which is desired to be utilized does not have the capability of swelling (increasing its size), is that the film may also include a loading of another particulate material which, itself, swells in the presence of a generally aqueous liquid. In some embodiments, particulates of the swellable material and the microbial adsorbent may be incorporated into the film in an agglomerated fashion so that each individual particle contains some of the non-swellable microbial adsorbent and some of the swellable material. In any of these embodiments the swellable material is one which can increase its volume at least 1.5 times in no more than 120 seconds. For example, the swellable material may be one which, in the presence of a generally aqueous fluid, increases its volume at least 1.5 times in no more than 60 seconds. More particularly, the swellable material may be one which, in the presence of a generally aqueous fluid, increases its volume at least 1.5 times in no more than 15 seconds. Even more particularly, the swellable material may be one which, in the presence of a generally aqueous fluid, increases its volume at least 2 times in no more than 1 second.

The microbial adsorbent may be any such adsorbent which is compatible with the film material being utilized. In some embodiments the microbial adsorbent may be a derivitized silane such as, for example, 3-(trimethoxysilyl) propyldimethyloctadecyl ammonium chloride. [$(CH_3)_3Si(CH_2)_3N^+(CH_3)_2C_{18}H_{37}Cl^-$]. This material was formerly available from the Dow Corning under the trade designation Dow Corning 5700. It now is available from Aegis Environmental. In other embodiments the microbial adsorbent is a heavy metal. For example, the heavy metal may be silver.

In other embodiments the microbial adsorbent may be a metallic salt. For example, the metallic salt may be a water-insoluble polyvalent metal salt. The water-insoluble polyvalent metal salt may be a salt of a metal selected from the group including Group IB, Group IIA, Group IIB, Group IIIA, Group IVB, Group VIB metals. More particularly, the metal may be selected from the group including iron, aluminum, lead, magnesium, silver, calcium and alloys of one or more of iron, aluminum, lead, magnesium, silver and calcium. The salt may be selected from the group including hydroxides, phosphates, chromates, oxides and peroxides. For example, the salt may be selected from the group including one or more of ferric hydroxides, ferrous hydroxides, aluminum hydroxides, magnesium hydroxide, magnesium oxide, magnesium peroxide, lead chromate and calcium hydroxide.

In some embodiments the microbial adsorbent may be selected from the group including colloidal clays. For example, the colloidal clay may be a bentonite such as sodium bentonite and/or calcium bentonite. The colloidal clay may, in some embodiments, be hectorite.

The microbial filter film of the present invention may be advantageously formed into a wide variety of items where it is desired to have a material which allows passage of, for example, water vapor but which prohibits the passage of microbes therethrough. For example, the item may be a garment, such as a surgical gown, foot protectors, face masks, head or hair coverings, aprons, jackets, pants, gloves, coveralls and, generally speaking, all clean room attire.

Alternatively there may be a product such as, for example, a sterile wrap material which is used to maintain the sterile field around a doctor's tools until they are utilized in an operation.

Likewise, the film of the present invention may conveniently be formed into a surgical drape for use on a patient during an operation.

DEFINITIONS

As used herein the term "breathable" refers to any material which has a water vapor transmission rate (WVTR) of at least 300 grams per square meter per 24 hours when measured in accordance with ASTM E 96-80.

As used herein the term "microbial adsorbent" refers to any material which has the ability to hold and/or inactivate microbes such as, for example, viruses, bacteria, cysts and/or nematodes on or near its surface.

As used herein the term "microporous passageway" refers to any passageway which, at some point along its length, has a diameter of fifty (50) microns or less.

As used herein the term "microporous film" refers to a film having a plurality of microporous passageways therethrough to make the film breathable. The microporous film will also have a hydrohead of at least 25 centimeters of water when its hydrohead is measured in accordance with Method 5514—Federal Test Methods Standard No. 191A. For example, the microporous film may have a hydrohead of at least 50 centimeters of water when so measured.

As used herein the term "generally aqueous liquid" refers to any liquid which has, as a major component, water. All bodily fluids including, without limitation, blood, saliva, menses, mucus, lymph fluid and urine, are expressly included within this definition.

Whether a material is "swellable" is determined by first providing 100 mL of water contained in a glass-stoppered cylinder of 100 mL capacity. Next a first two (2) gram portion of the material is dropped onto the surface of the water and allowed to completely settle. Then, a second two (2) gram portion of the material being tested is dropped onto the surface. After two (2) hours, the volume occupied by the material at the bottom of the cylinder is observed. For a material to be "swellable", the material at the bottom of the cylinder must have an apparent volume of not less than 6 mL.

As used herein, the term "nonwoven web" refers to a web that has a structure of individual fibers or filaments which are interlaid, but not in an identifiable repeating manner.

As used herein the term "spunbond fibers" refers to fibers which are formed by extruding molten thermoplastic material as filaments from a plurality of fine, usually circular capillaries of a spinnerette with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. Nos. 3,502,763 and 3,909,009 to Levy, and U.S. Pat. No. 3,542,615 to Dobo et al. which are all herein incorporated by reference.

As used herein the term "meltblown fibers" means fibers formed by extruding a molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers. Meltblowing is described, for example, in U.S. Pat. No. 3,849,241 to Buntin, U.S. Pat. No. 4,307,143 to Meitner et al., and U.S. Pat. No. 4,707,398 to Wisneski et al. which are all herein incorporated by reference.

BRIEF DESCRIPTION OF THE DRAWINGS

FIG. 2 illustrates the embodiment in the configuration where the physical barrier has been formed.

DETAILED DESCRIPTION OF THE INVENTION

Figure 1:
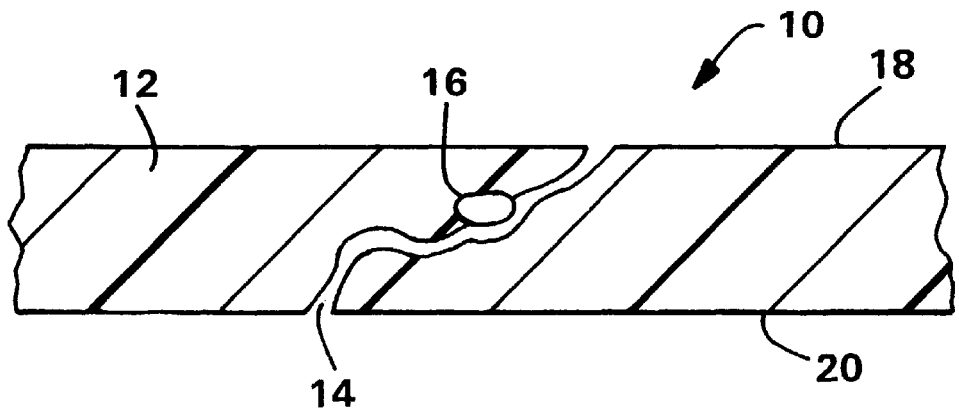
FIG. 1 is a schematic, highly enlarged cross-sectional view of a breathable, microbial barrier film designed in accordance with the teachings of the present invention.

Turning now to the drawings where like reference numerals represent like or equivalent structures or process steps, an improved microporous film 10 of the present invention is depicted. Typically, the film 10 will be formed from a sheet 12 of a thermoplastic material. For purposes of simplicity and clarity the film 10 is depicted as having only one microporous passageway 14. However, those of ordinary skill in the art will readily recognize that typical microporous films 10 possess a multitude of such passageways 14 per square inch. The film 10 is configured so that a particle 16 of a material which is a microbial adsorbent is positioned at some point along the length of the passageway between the first surface 18 of the film 10 and the second surface 20 of the film 10. In most instances, the passageways 14 will be sized in such a manner as to allow the passage of water vapor through the film 10. That is, the film 10 is breathable. In particular, a portion of the microporous passageway 14 is defined by the microbial adsorbent 16 so that microbes (not illustrated) attempting to pass through the film 10 via a passageway 14 must pass in close proximity to the microbial adsorbent 16. This arrangement allows the microbial adsorbent 16 to interdict microbes by adsorbing them and prohibiting their passage through the film 10 while still retaining the breathability of the film 10.

In some embodiments the thermoplastic material 12 may be selected from the group including polyolefins, polyamides, polyesters and copolymers and blends in any combination of these and/or any other suitable material. For example, the polyolefin may be selected from the group consisting of polypropylenes, polyethylenes, polybutylenes and copolymers and blends thereof. The polyethylene may be linear low density polyethylene.

By specifically tailoring the type of microbial adsorbent 16 present in the film 10, the film 10 may be adapted to adsorb a wide variety of pathogens. For example, the film 10 may be tailored to act as a filter for viruses, bacteria, cysts and/or nematodes. Naturally the film 10 may be adapted to adsorb specific types of viruses, bacteria, cysts and/or nematodes depending upon the use to which it is to be assigned. Utilization of a pathogen-specific adsorbent readily accomplishes this result.

Figure 2:
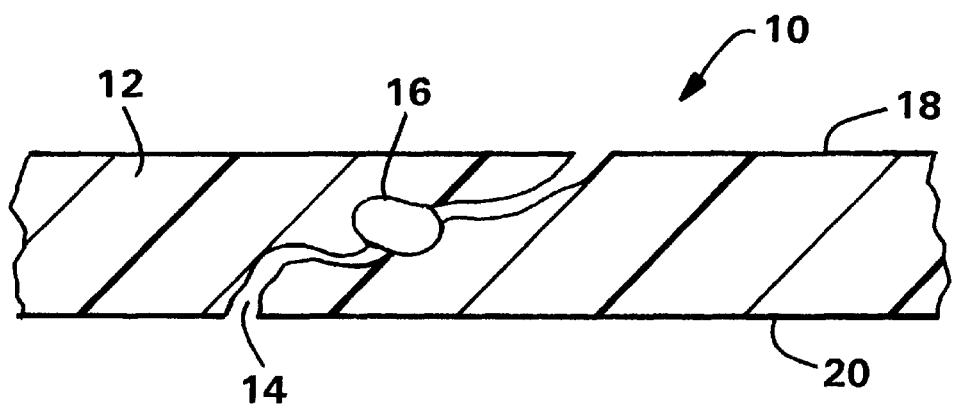
FIG. 2 is a schematic, highly enlarged cross-sectional view of an embodiment of a breathable, microbial barrier film designed in accordance with the teachings of the present invention and where the film also forms a physical barrier to the passage of liquids at the site of contact of the film by such a liquid.

In certain embodiments, the film 10 may be designed to not only act as a filter (adsorbent) for microbes as a result of the presence of the microbial adsorbent 16, but may also be designed to act as a physical (mechanical) barrier to fluids attempting to pass therethrough. To this end, the microbial adsorbent 16 utilized may be a swellable one which, in the presence of a generally aqueous fluid, to increase its volume at least 1.5 times in no more than 120 seconds. For example, the microbial adsorbent 16 may be one which, in the presence of a generally aqueous fluid, increases its volume at least 1.5 times in no more than 60 seconds. More particularly, the microbial adsorbent 16 may be one which, in the presence of a generally aqueous fluid, increases its volume at least 1.5 times in no more than 15 seconds. Even more particularly, the microbial adsorbent 16 may be one which, in the presence of a generally aqueous fluid, increases its volume at least 2 times in no more than 1 second. In the event such a microbial adsorbent 16 is utilized, the adsorbent 16 will, upon being contacted with the generally aqueous fluid, increase in size and swell. The swelling serves to block the microporous passageway 14 which is in close proximity to the swellable adsorbent 16. Blockage of the passageway 14 creates a physical barrier within the microporous passageway 14 with the consequence that no liquid can pass therethrough. Thus, a physical or mechanical barrier (dam) is formed in the passageway 14 which closes off the passageway 14. FIG. 2 illustrates an embodiment of the present invention where the microbial adsorbent 16 is swellable and has swollen to seal off or dam up the passageway 14. This arrangement results in a "smart" film 10 in that the film 10 reacts to its being contacted by a liquid only in the area where the liquid contact occurs. Therefore, the film 10 remains breathable because of the presence of numerous other micropores 14 which have not been blocked. A specific example of a swellable microbial adsorbent is bentonite and, in particular, sodium bentonite.

Figure 3:
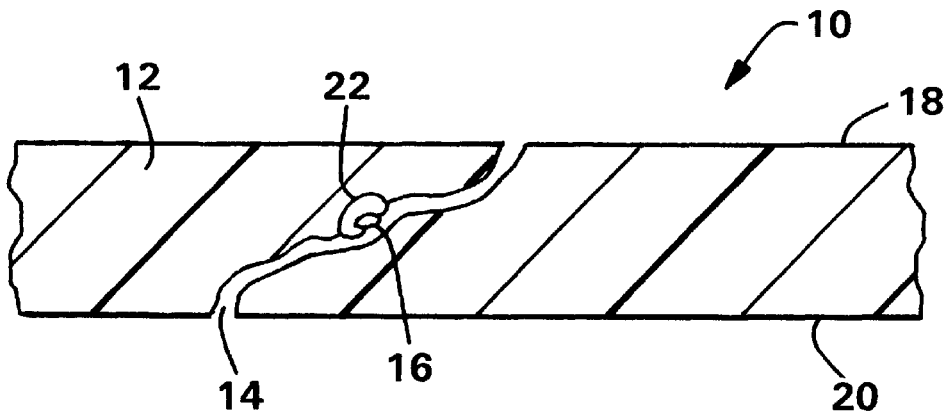
FIG. 3 is a schematic, highly enlarged cross-sectional view of another embodiment of a breathable, microbial barrier film designed in accordance with the teachings of the present invention and where the film forms a physical barrier to the passage of liquids at the site of contact of the film by a liquid.

An alternative manner by which physical blockage of the passageway 14 may be obtained, if the microbial adsorbent 16 which is desired to be utilized does not have the capability of swelling (increasing its size), is that the film 10 may also include a loading of another particulate material 22 which, itself, swells in the presence of a generally aqueous liquid. In some embodiments, particulates of the swellable material 22 and the microbial adsorbent 16 may be incorporated into the film 10 in an agglomerated fashion so that each individual particle contains some of the non-swellable microbial adsorbent 16 and some of the swellable material 22. In any of these embodiments the swellable material 22 is one which can increase its volume at least 1.5 times in no more than 120 seconds. For example, the swellable material 22 may be one which, in the presence of a generally aqueous fluid, increases its volume at least 1.5 times in no more than 60 seconds. More particularly, the swellable material 22 may be one which, in the presence of a generally aqueous fluid, increases its volume at least 1.5 times in no more than 15 seconds. Even more particularly, the swellable material 22 may be one which, in the presence of a generally aqueous fluid, increases its volume at least 2 times in no more than 1 second. Specific examples of such swellable materials 22 which may be utilized in conjunction with a non-swelling microbial adsorbent 16 include, without limitation, kaolins and diatomaceous earth. The diatomaceous earth may be treated, as is known to those in the art, so as to be positively charged. One constraint in this design is that the microbial adsorbent 16 and the swellable material 22 must both be exposed to the passageway 14 for each to perform their respective functions. Such a design is schematically illustrated in FIG. 3.

The microbial adsorbent 16 may be any such adsorbent 16 which is compatible with the film material 12 being utilized. In some embodiments the microbial adsorbent 16 is a heavy metal. For example, the heavy metal may be silver.

In other embodiments the microbial adsorbent 16 may be a metallic salt. For example, the metallic salt may be a water-insoluble polyvalent metal salt. The water-insoluble polyvalent metal salt may be a salt of a metal selected from the group including Group IB, Group IIA, Group IIB, Group IIIA, Group IVB, Group VIB metals. More particularly, the metal may be selected from the group including iron, aluminum, lead, magnesium, silver, calcium and alloys of one or more of iron, aluminum, lead, magnesium, silver and calcium. The salt may be selected from the group including hydroxides, phosphates, chromates, oxides and peroxides. For example, the salt may be selected from the group including one or more of ferric hydroxides, ferrous hydroxides, aluminum hydroxides, magnesium hydroxide, magnesium oxide, magnesium peroxide, lead chromate and calcium hydroxide.

In some embodiments the microbial adsorbent 16 may be selected from the group including colloidal clays. For example, the colloidal clay may be a bentonite such as sodium bentonite and/or calcium bentonite. In some embodiments the colloidal clay may be a hectorite.

The microbial filter film 10 of the present invention may be advantageously formed into a wide variety of items where it is desired to have a material which allows passage of, for example, water vapor but which prohibits the passage of microbes therethrough. For example, the item may be a garment such as a surgical gown, foot protectors, face masks, head or hair coverings, aprons, jackets, pants gloves, coveralls and, generally speaking, all clean room attire.

Alternatively the film 10 may be incorporated into a product such as, for example, a sterile wrap material which is used to maintain the sterile field around a doctor's tools until they are utilized in an operation.

Likewise, the film 10 of the present invention may conveniently be formed or incorporated into a surgical drape for use on a patient during an operation.

The film 10 of the present invention may be made by a wide variety of methods known to those of skill in the art. One method of forming the film 10 is described in detail in U.S. patent application Ser. No. 08/254,207 entitled "Stretch-Thinned Film and Nonwoven Laminate" and filed on Jun. 6, 1994 in the names of Ann Louise McCormack, Lance James Garrett, Jr. and Karen Lynn English. This application is hereby specifically incorporated by reference into the present application in its entirety. It is known that films can be made to be breathable by adding filler particles such as calcium carbonate to the film during the film-forming process. Once the particle-filled film has been formed by conventional methods, it is then either stretched or crushed to create passageways therethrough. This action results in the creation of a breathable film. This particular method also results in a configuration where at least one of the particles defines a portion of substantially every passageway. Accordingly, this method is well suited for the formation of the films 10 in accordance with the present invention. These films 10 can be readily manufactured by substituting particles of the microbial adsorbent 16 for the filler material. All other process steps remain essentially the same. Of course, the microbial adsorbent 16 selected desirably will not chemically interfere with or adversely affect the extruded film 10 and will have the ability to be relatively uniformly dispersed throughout the film 10. For example, the moisture content of the microbial adsorbent 16 should be maintained at 1%, by weight, or less for satisfactory extrusion to occur. Generally speaking, the microbial adsorbent 16 particles will have an average particle size in the range of from about 0.1 to about 7 microns. Of course, the maximum size particle which may be utilized will be related to the ultimate thickness (thinness) of the film 10. Typically the film 10 will contain at least about 30%, by weight of the film, of the adsorbent 16.

As has been previously stated, in some embodiments, it may be desirable to form a laminate of the film 10 of the present invention and one or more nonwoven webs. Such a laminate would have a cloth-like appearance and feel, be breathable like cloth and still would be able to prevent the passage of microbes therethrough.

Figure 4:
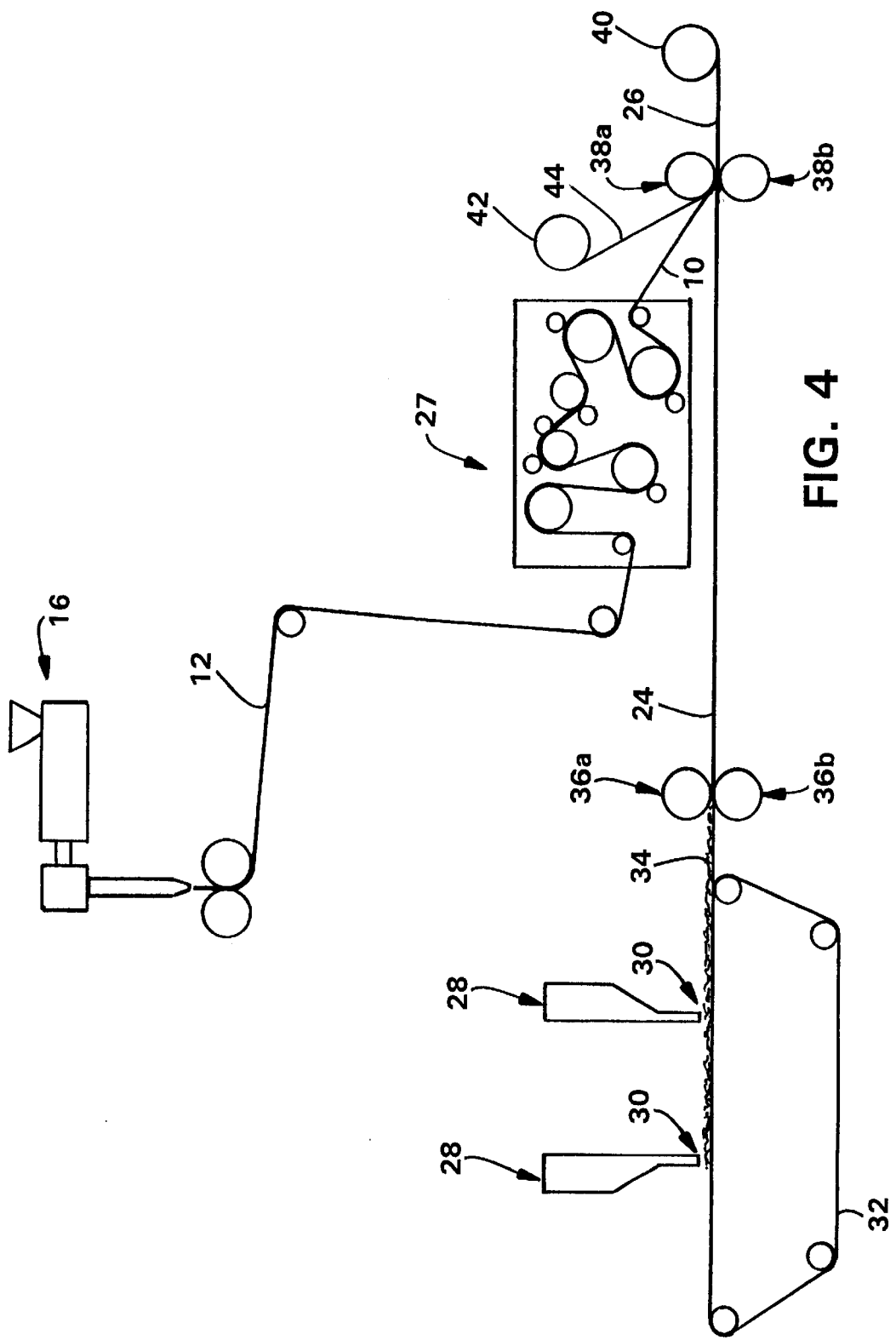
FIG. 4 is a schematic representation of a process for forming a laminate having the breathable, microbial barrier film of the present invention incorporated therein.

FIG. 4 schematically illustrates a process for forming such a laminate by forming a stretch-thinned film 10 and an nonwoven web 24 into a laminate 26. The film 10 is formed using any type of conventional film forming equipment such as cast or blown equipment. Prior to extrusion, the film-forming material is filled with the microbial adsorbent 16 in particulate form. After conventional formation of the film 10, it is sent through a film stretching apparatus to stretch and thin the film to an appropriate thickness which is on the order of 0.55 mils or less. The stretch-thinning step also creates the micropores or passageways 14 through the film 10 as is well known to those of skill in the art. One type of apparatus for such stretch-thinning is a Machine Direction Orienter 27 (MDO) Unit, Model No. 7200 from the Marshall and Williams Company of Providence, R.I.

FIG. 4 also illustrates that while the film layer 10 is being formed and thinned, the fibrous nonwoven web 24 is also being formed. Conventional fibrous nonwoven web 24 forming apparatus 28, such as a spunbond machine, may be used to form the web 24. The long, essentially continuous spunbonded fibers 30 are deposited onto a forming wire 32 as an unbonded matt 34 and the unbonded matt 34 is then sent through a pair of bonding rolls 36a, 36b to bond the fibers 30 together and increase the tear strength of the resultant web 24. One or both of the rolls 36a, 36b are often heated to aid in bonding. Typically, one of the rolls 36a is also patterned so as to impart a discrete bond pattern with a prescribed bond surface area to the web 24. The other roll 36b is usually a smooth anvil roll but this roll 36b may also be patterned if so desired.

Once the film 10 has been sufficiently thinned and oriented and the nonwoven web 24 has been formed, the two layers are brought together and laminated to one another using a pair of laminating rolls or other means 38a, 38b. As with the bonding rolls 36a, 36b, the laminating rolls 38a, 38b may be heated. Also, at least one of the rolls 38a may be patterned to create a discrete bond pattern with a prescribed bond surface area for the laminate 26. Generally, the maximum bond point surface area for a given area of surface on one side of the laminate 26 will not exceed about 60 percent of the total surface area.

After the laminate 26 has been formed, it is wound into a roll 40 for subsequent processing. Alternatively, the laminate 26 may continue in-line for further conversion into other items or products.

It should be noted that this process may be altered in a number of ways without departing from the spirit and scope of the present invention. For example, a different apparatus can be used for stretch-thinning the film 10. Different film/nonwoven web forming equipment such as meltblown and bonded carded web equipment may be used in place of the spunbond equipment. In addition, other means for bonding and laminating may be used provided the resultant laminate has the required properties described herein. Lastly, the formation processes for making the film and support layers may be done at a remote site and rolls of the two materials may be unwound into the process.

The process shown also may be used to create a three layer laminate. By modifying the previously described process to feed a supply 42 of a second fibrous nonwoven web 44 into the laminating rolls 38a, 38b on a side of the film 10 opposite that of the first fibrous nonwoven web 24. As shown in FIG. 4, the supply of material for the second fibrous nonwoven web 44 is in the form of a preformed roll 42. As with the other layers 10 and 24, layer 42 may be formed directly in-line or it may be preformed and then fed into the process from a supply roll. In either event, the second nonwoven web 44 is fed into the laminating rollers 38a, 38b and is laminated to the film 10 in the same fashion as nonwoven web 24.

Figure 5:
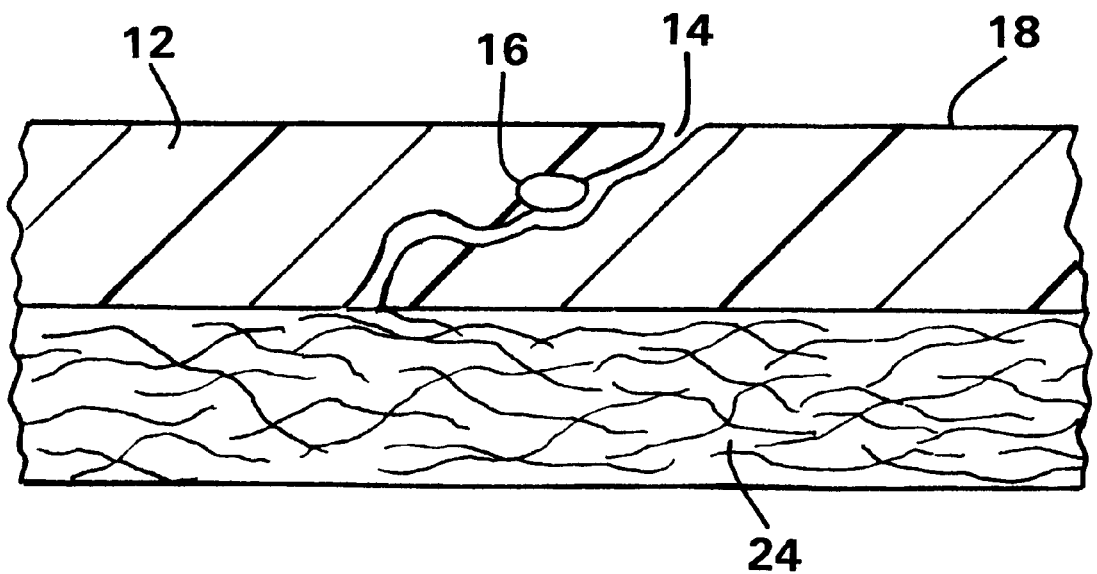
FIG. 5 is a schematic, highly enlarged cross-sectional view of a laminate of a nonwoven web and the breathable, microbial barrier film of FIG. 1.

FIG. 5 is a schematic, highly enlarged cross-sectional view of a two-layer laminate of a nonwoven web 24 and a film 10 made in accordance with the present invention. For purposes of clarity and simplicity, only one micropassageway 14 in the film 10 is illustrated. Those of skill in the art will readily recognize that conventional microporous films will contain a plethora of such passageways on a per square inch or per square centimeter basis. For example, from about 100 to 100,000 or more passageways per square centimeter may be present.

It is to be understood that variations and modifications of the present invention may be made without departing from the scope of the invention. It is also to be understood that the scope of the present invention is not to be interpreted as limited to the specific embodiments disclosed herein, but only in accordance with the appended claims when read in light of the foregoing disclosure.

What is claimed is:

1. A film including a microbial adsorbent, the film comprising:

a first surface; and a second surface;

with the film defining at least one microporous passageway allowing communication through the film between the first and second surfaces;

wherein a portion of the microporous passageway is defined by the microbial adsorbent, and wherein said film further includes a swellable material defining at least a portion of the microporous passageway, said swellable material being capable, in the presence of a liquid, of increasing its volume to such an extent that the passage of the aqueous fluid through said microporous passageway is substantially inhibited.

2. The film according to claim 1, wherein the film is formed from at least one material selected from the group consisting of polyolefins, polyamides, polyesters and copolymers and blends in any combination of these.

3. The film according to claim 2, wherein the polyolefin is selected from the group consisting of polypropylenes, polyethylenes, polybutylenes and copolymers and blends thereof.

4. The film according to claim 3, wherein the polyethylene is linear low density polyethylene.

5. The film according to claim 1, wherein the microbial adsorbent is adapted to adsorb at least one type of virus.

6. The film according to claim 1, wherein the microbial adsorbent is adapted to adsorb at least one type of bacteria.

7. The film according to claim 1, wherein the microbial adsorbent is adapted to adsorb at least one type of cyst.

8. The film according to claim 1, wherein the microbial adsorbent is adapted to adsorb at least one type of nematode.

9. A film including a microbial adsorbent, the film comprising:

a first surface; and a second surface;

with the film defining at least one microporous passageway allowing communication through the film between the first and second surfaces;

wherein a portion of the microporous passageway is defined by the microbial adsorbent and wherein said microbial adsorbent is capable, in the presence of a liquid, of increasing its volume to such an extent that the passage of the liquid through said microporous passageway is substantially inhibited.

10. The film according to claim 9 wherein the microbial adsorbent is capable, in the presence of a generally aqueous fluid, of increasing its volume at least 1.5 times in no more than 120 seconds.

11. The film according to claim 9, wherein the microbial adsorbent is capable, in the presence of a generally aqueous fluid, of increasing its volume at least 1.5 times in no more than 60 seconds.

12. The film according to claim 9, wherein the microbial adsorbent is capable, in the presence of a generally aqueous fluid, of increasing its volume at least 1.5 times in no more than 15 seconds.

13. The film according to claim 9, wherein the microbial adsorbent is capable, in the presence of a generally aqueous fluid, of increasing its volume at least 2 times in no more than 1 second.

14. The film according to claim 1, wherein said swellable material which defines a portion of the passageway is capable, in the presence of a generally aqueous fluid, of increasing its volume at least 1.5 times in no more than 120 seconds.

15. The film according to claim 1, wherein said swellable material which defines a portion of the passageway is capable, in the presence of a generally aqueous fluid, of increasing its volume at least 1.5 times in no more than 60 seconds.

16. The film according to claim 1, wherein said swellable material which defines a portion of the passageway is capable, in the presence of a generally aqueous fluid, of increasing its volume at least 1.5 times in no more than 15 seconds.

17. The film according to claim 1, wherein said swellable material which defines a portion of the passageway is capable, in the presence of a generally aqueous fluid, of increasing its volume at least 2 times in no more than 1 second.

18. The film according to claim 14, wherein the microbial adsorbent is attached to the swellable material.

19. The film according to claim 1, wherein the microbial adsorbent is a heavy metal.

20. The film according to claim 19, wherein the heavy metal is silver.

21. The film according to claim 1, wherein the microbial adsorbent is a metallic salt.

22. The film according to claim 21, wherein the metallic salt is a water-insoluble polyvalent metal salt.

23. The film according to claim 22, wherein the water-insoluble polyvalent metal salt is a salt of a metal selected from the group consisting of Group IB, Group IIA, Group IIB, Group IIIA, Group IVB, Group VIB metals.

24. The film according to claim 23, wherein the metal is selected from the group consisting of at least one of iron, aluminum, lead, magnesium, silver, calcium and alloys of one or more of iron, aluminum, lead, magnesium, silver and calcium.

25. The film according to claim 22, wherein the salt is selected from the group consisting of hydroxides, phosphates, chromates, oxides and peroxides.

26. The film according to claim 25, wherein the salt is selected from the group consisting of one of more of ferric hydroxides, ferrous hydroxides, aluminum hydroxides, magnesium hydroxide, magnesium oxide, magnesium peroxide, lead chromate and calcium hydroxide.

27. The film according to claim 1, wherein the microbial adsorbent is selected from the group consisting of colloidal clays.

28. The film according to claim 27, wherein the colloidal clay is selected from the group consisting of bentonite and hectorite.

29. The film according to claim 28, wherein the bentonite is sodium bentonite.

30. The film according to claim 28, wherein the bentonite is calcium bentonite.

31. An item comprising the film according to claim 9.

32. The item according to claim 31, wherein the item is a garment.

33. The garment according to claim 32, wherein the garment is suitable for clean room attire.

34. The garment according to claim 32, wherein the garment is selected from the group consisting of a surgical gown, foot protectors, face masks, head or hair coverings, aprons, jackets, pants, gloves and coveralls.

35. The item according to claim 31, wherein the item is a sterile wrap.

36. The item according to claim 31, wherein the item is a surgical drape.

37. A laminate of the film of claim 9 and a nonwoven web.

38. A film including a microbial adsorbent, the film comprising:

a first surface; and a second surface;

with the film defining at least one microporous passageway allowing communication through the film between the first and second surfaces;

wherein a portion of the microporous passageway is defined by the microbial adsorbent, and wherein said microbial adsorbent is selected from the group consisting of colloidal clays.

39. The film according to claim 38, wherein the colloidal clay is selected from the group consisting of bentonite and hectorite.

40. The film according to claim 39, wherein the bentonite is sodium bentonite.

41. The film according to claim 39, wherein the bentonite is calcium bentonite.

\* \* \* \* \*